United States Patent
Tsao et al.

(10) Patent No.: US 8,420,076 B2
(45) Date of Patent: *Apr. 16, 2013

(54) **THERAPY OR PROPHYLAXIS OF *KLEBSIELLA PNEUMONIAE* INFECTIONS WITH A LYTIC BACTERIOPHAGE SPECIFICALLY AGAINST THE *K. PNEUMONIAE***

(75) Inventors: Nina Tsao, Kaohsiung (TW); Chih-Feng Kuo, Kaohsiung (TW); Chih-Hsin Hung, Kaohsiung (TW)

(73) Assignee: I-Shou University, Dashu Township, Kaohsiung County (TW)

( * ) Notice: Subject to any disclaimer, the term of this patent is extended or adjusted under 35 U.S.C. 154(b) by 44 days.

This patent is subject to a terminal disclaimer.

(21) Appl. No.: 12/986,917

(22) Filed: Jan. 7, 2011

(65) Prior Publication Data
US 2011/0217268 A1    Sep. 8, 2011

(30) Foreign Application Priority Data
Mar. 2, 2010 (TW) ................................ 99105991 A

(51) Int. Cl.
*C12N 7/00* (2006.01)
*A01N 63/00* (2006.01)

(52) U.S. Cl.
USPC ........................... 424/93.6; 435/5; 435/235.1

(58) Field of Classification Search .................. 424/93.6
See application file for complete search history.

(56) References Cited

U.S. PATENT DOCUMENTS

| | | | |
|---|---|---|---|
| 5,811,093 A * | 9/1998 | Merril et al. | 424/93.6 |
| 7,622,293 B2 | 11/2009 | Sulakvelidze et al. | |
| 7,635,584 B2 | 12/2009 | Sulakvelidze et al. | |
| 7,674,467 B2 | 3/2010 | Sulakvelidze et al. | |
| 7,745,194 B2 | 6/2010 | Pasternack et al. | |
| 2011/0217756 A1 * | 9/2011 | Tsao et al. | 435/235.1 |

OTHER PUBLICATIONS

Lederman ER, Crum NF. Pyogenic liver abscess with a focus on *Klebsiella pneumoniae* as a primary pathogen: an emerging disease with unique clinical characteristics. Am J Gastroenterol. Feb. 2005;100(2):322-31.*

Jensen, E.C., Schrader H.S., Rieland B., Thompson T.L., Lee K.W., Nickerson, K.W., and Kokjohn, T.A., "Prevalence of Broad-Host-Range Lytic Bacteriophages of *Sphaerotilus natans*, *Escherichia coli*, and *Pseudomonas aeruginosa*," Applid and Enviromental Microbiology, Feb. 1998, p. 575-580.

Langley R., Kenna, D.T., Vandamme, P., Ure R., and Govan J.R.W.,"Lysogeny and Bateriophage host range within the *Burkholderia cepacia* complex," Journal of Medical Microbiology (2003), 52, 483-490.

* cited by examiner

*Primary Examiner* — Kevin Hill
*Assistant Examiner* — Arthur S Leonard
(74) *Attorney, Agent, or Firm* — Muncy, Geissler, Olds & Lowe, PLLC

(57) ABSTRACT

A therapy or prophylaxis of *K. pneumoniae* infections with a lytic bacteriophage specifically against *K. pneumoniae*, provides a lytic bacteriophage (DSM 24329) to a *K. pneumoniae* infected organism for the sake of relieving the serious complications of liver abscesses and bacteremia, and the high mortality rate of *K. pneumoniae* infections in Taiwan.

6 Claims, 6 Drawing Sheets

FIG. 2

THERAPY OR PROPHYLAXIS OF KLEBSIELLA PNEUMONIAE INFECTIONS WITH A LYTIC BACTERIOPHAGE SPECIFICALLY AGAINST THE K. PNEUMONIAE

BACKGROUND OF THE INVENTION

1. Field of the Invention

The present invention relates to a therapy or prophylaxis of *Klebsiella pneumoniae* infections, particularly to a therapy or prophylaxis of *K. pneumoniae* infections with a newly isolated lytic bacteriophage specifically against the *K. pneumoniae*.

2. Description of the Related Art

*Klebsiella pneumoniae*, belonging to the family of Enterobacteriaceae and the genus of *Klebsiella*, is a gram-negative bacterium widely found in the normal flora of the intestinal and respiratory tracts of humans. However, the *K. pneumoniae* is also a significant opportunistic pathogen, usually causing severe diseases such as pneumonia in immunocompromised individuals, children or nosocomial patients. In clinical medicine, *K. pneumoniae* infections are primary characteristics of liver necrosis, urinary inflammation and septicemia. Once the patients have been diagnosed, a proper treatment must be given straightaway to avoid the serious complications and high mortality risks of *K. pneumoniae* infections.

Traditionally, the treatment of *K. pneumoniae* infections is mainly based on antibiotics, such as aminoglycosides (including gentamicin, tobramycin and amikacin) and cephalosporins. Nevertheless, due to occurrences of multiple drug-resistant strains currently, the therapy of *K. pneumoniae* infections has become both more difficult and essential. On the other hand, an increasing amount of *K. pneumoniae* infected patients in Taiwan have developed serious complications such as pyogenic liver abscess, metastatic meningitis and endophthalmitis, particular to diabetes mellitus and chronic respiratory cases. In these situations, around a 10~30% rate of mortality has been experienced, and serious sequelae may arise, even if the patient is given proper antibiotic treatment.

As reported by recent researches, several genetic loci of the *K. pneumoniae* have been identified as virulence genes, and it is suggested that virulence factors encoded from the virulence genes show strong resistance to human immune system, being significantly invasive during infection. As a result, conventional therapy and prophylaxis may be ineffective in relieving *K. pneumoniae* infections in Taiwan.

Bacteriophages, also known as phages, are viruses that infect bacteria. These viruses may rapidly attach, penetrate and immediately reproduce in the target bacteria followed by lyse and release from the bacterial cell, which can be an alternative therapeutic strategy for *K. pneumoniae* infections. It has been reported that the bacteriophage treatment is sufficient to suppress the infections of *Staphylococcus aureus*, *Escherichia coli* and *Pseudomonas aeruginosa* in some western countries. Through the bacteriophage treatment, the therapy of bacterial infections can be achieved more economically and effectively, with no risk of drug-resistance or safety issues. Thus, regarding the severity of *K. pneumoniae* infections and its complications in Taiwan, there is an urgent need of providing a new therapy or prophylaxis of *K. pneumoniae* infections with a lytic bacteriophage specifically against the invasive *K. pneumoniae* in Taiwan.

SUMMARY OF THE INVENTION

The primary objective of this invention is to provide a therapy of *K. pneumoniae* infections with a lytic bacteriophage specifically against *K. pneumoniae*, which can significantly relieve *K. pneumoniae* infections so as to reduce the serious complications thereof, such as liver abscesses and bacteremia.

A therapy of *K. pneumoniae* infections with a lytic bacteriophage specifically against *K. pneumoniae*, provides a lytic bacteriophage (DSM 24329) to an living organism to treat *K. pneumoniae* infected patients, for the sake of avoiding the serious complications of liver abscesses and bacteremia, and decreasing, the high mortality rate of *K. pneumoniae* infections.

Further scope of the applicability of the present invention will become apparent from the detailed description given hereinafter. However, it should be understood that the detailed description and specific examples, while indicating preferable embodiments of the invention, are given by way of illustration only, since various more will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 2 shows histochemistry stain data of liver tissue in infected mice;

In the various figures of the drawings, the same numerals designate the same or similar parts.

DETAILED DESCRIPTION OF THE INVENTION

Figure 1:
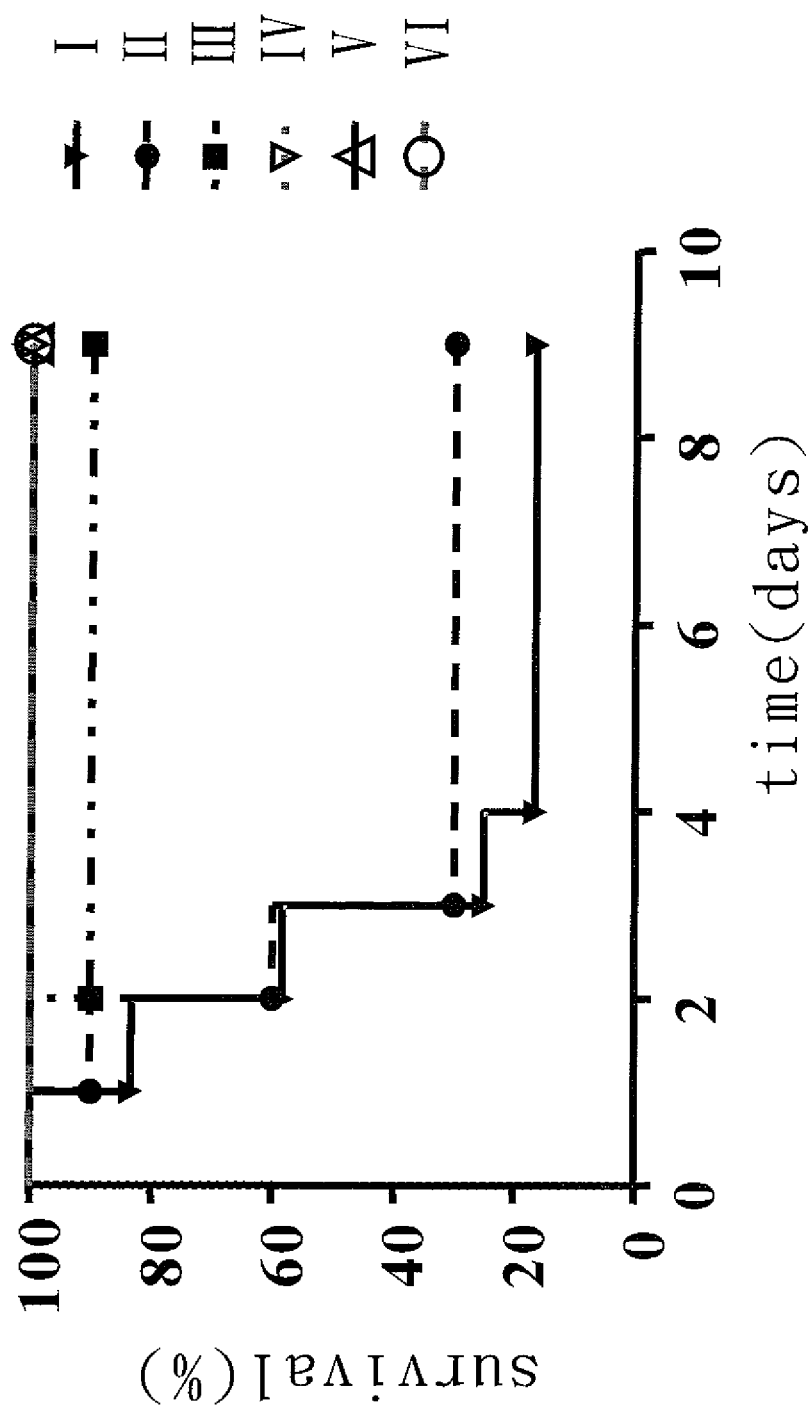
FIG. 1 is a line chart illustrating the survival rate of mice with different intraperitoneal dosages of bacteriophage treatment.

The present invention relates to a therapy or prophylaxis of *K. pneumoniae* infections with a lytic bacteriophage specifically against *K. pneumoniae*, which provides a newly isolated lytic bacteriophage (DSM 24329) to a living organism for the sake of relieving the serious complications of liver abscesses and bacteremia, and the high mortality rate of *K. pneumoniae* infections in Taiwan.

The lytic bacteriophage of the present invention, has been deposited on 10 Dec. 2012 at DSMZ-Deutsche Sammlung von Mikroorganismen and Zellkulturen, which has an address of Inhoffenstrasse 7B, 38124, Braunschweig, Germany. This lytic bacteriophage with the deposit number DSM 24329, has been proved to show broad host range to and lytic effects on *K. pneumoniae* in Taiwan, whether in in vivo or in vitro models.

In the embodiment of the present invention, the lytic bacteriophage of the present invention is obtained via an isolation program comprising a step of "isolation" and a step of "selection", which is classified as a phage of *Podoviridae* in comparison with the morphological and genetic information in the Database of the International Committee on Taxonomy of Virus, also named ICTVdB.

In the step of "isolation," the bacteriophage of the present invention is isolated from sewage of the E-Da Hospital in Taiwan. First, a procedure of bacteriophage enrichment is performed by removing the dust, debris and germs in the sewage via a process of centrifugation at 14170×g for 15 minutes and a process of filtration with a filter of 0.22 μl, and further mixing up the sewage with a LB broth medium containing a clinical strain of $K.$ $pneumoniae$ (deposited at DSMZ-Deutsche Sammlung von Mikroorganismen and Zellkulturen with deposit number DSM 24328). In the present invention, the clinical strain of $K.$ $pneumoniae$ (DSM 24328) is collected from a patient in a Taiwanese hospital who has serious $K.$ $pneumoniae$ infection and complications of liver abscess and bacteremia. The sewage and the culture medium are co-incubated at 37° C. for about 12 hours to obtain a mixture. In this situation, the bacterial bacteriophages in the sewage will randomly adhere to the $K.$ $pneumoniae$ cells for infection and proliferation. Next, the mixture is extracted with chloroform (32 μl/ml), in order to lyse the $K.$ $pneumoniae$ cell and release the reproduced bacteriophages. Finally, the mixture is centrifuged at 14170×g for another 15 minutes, to remove the bacterial dregs and collect a bacteriophage supernatant from the mixture.

In the step of "selection," a bacteriophage with specific lysis effect on $K.$ $pneumoniae$ cells is selected. Precisely, the bacteriophage is selected according to a plaque assay published by Jensen et. al. in 1998. The prepared bacteriophage lysate supernatant and an overnight culture of $K.$ $pneumoniae$ cells in a ratio of 1:1 volume, are mixed in 5 ml of soft agar (such as LB-soft agar), and poured on an agar-medium plate, for example a LB agar-plate, for overnight culturing. Then, a plurality of single plaques harvested on the medium plate will be collected and diluted with a buffer, such as a phosphate buffer. In the present invention, the diluted plaques are further mixed up with the overnight culture of $K.$ $pneumoniae$ cells and follow above steps to purified bacteriophage, and the above plaque assay is repeated for at least 3 times, finally to obtain a pure strain of bacteriophage.

In this step, the bacteriophage (DSM 24329) of the present invention (with $2 \times 10^9$ PFU/ml) is further amplified in $K.$ $pneumoniae$ cells according to a reproducing method reported by Langley et al. in 2003, by co-incubating with 5 times the volume of $K.$ $pneumoniae$ cells (with $2 \times 10^8$ CFU/ml) and 50 times the volume of LB-soft agar, and pouring on a LB medium plate for 6 hours culturing. Then, clear plaques harvested on the LB medium plate will be taken and extracted by adding a PBS buffer for overnight incubation at 4° C. The PBS buffer from the medium plate further undergoes a process of centrifugation at 14170×g for 30 minutes, filtration with 0.22 μl of filter, and incubation with DNase I for 1 hour sequentially to completely exclude the debris, germs and bacterial nucleic acid and obtain a bacteriophage suspension. Next, polyethylene glycol 8000 (PEG-8000; Sigma) and NaCl are added separately to the bacteriophage suspension to provide the final concentration of 3% PEG-8000 and 0.33M respectively, followed by keeping at 4° C. for 1 hour and centrifugation at 4° C., 14170×g for 30 minutes to take the precipitation of the bacteriophage suspension. As a result, the purified bacteriophage of the present invention will finally be obtained via a repeated process of CsCl gradient separation by loading the precipitation on top of the CsCl gradient (1.3, 1.5 or 1.7 g/ml), centrifuging at 35000 rpm at 4° C. for 9 hours and dialyzing with a PBS buffer, and a process of a Detoxi-Gel™ endotoxin removing gel for removing the remaining endotoxins.

To further indicate the benefits of the therapy or prophylaxis of $K.$ $pneumoniae$ infections with the bacteriophage (DSM 24329) in the present invention, C57BL/6 mice are prepared and inoculated with an invasive strain of $K.$ $pneumoniae$, and the pathological changes occurring on C57BL/6 mice are monitored and recorded, including damages of liver functions, bacteremia and mortality. In the embodiment of the present invention, the invasive strain of $K.$ $pneumoniae$ is obtained from a Taiwanese patient with $K.$ $pneumoniae$ infection complicated by primary liver abscess and bacteremia at the National Cheng-Kung University Hospital in Taiwan, and deposited at DSMZ-Deutsche Sammlung von Mikroorganismen and Zellkulturen with deposit number DSM 24328.

As summarized in Table 1, the bacteriophage (DSM 24329) of the present invention is inoculated to 6 groups of mice having had intragastric treatment of $K.$ $pneumoniae$ (DSM 24328) in advance, comprising a group of negative control (labeled as I) with $K.$ $pneumoniae$ infection only, a group of positive control (labeled as VI) with bacteriophage treatment only via intraperitoneal injection, and groups II to V sharing the $K.$ $pneumoniae$ infection and different doses of bacteriophage treatment via intraperitoneal injection. In this embodiment, the mortality (see the FIG. 1), liver functions including tissue histochemistry (see FIG. 2 and FIG. 3), AST assay (see the FIG. 4), ALT assay (see the FIG. 5) and bacterial count (see the Table 2) in each group of mice are analyzed and discussed during the test.

TABLE 1

The titer of $K.$ $pneumoniae$ (DSM 24328) and bacteriophage (DSM 24329) in each group

| Groups | MOI of the bacteriophage | Titer of $K.$ $pneumoniae$ (CFU/mouse) |
| --- | --- | --- |
| I | — | $2 \times 10^8$ |
| II | 0.001 | $2 \times 10^8$ |
| III | 0.01 | $2 \times 10^8$ |
| IV | 0.1 | $2 \times 10^8$ |
| V | 1 | $2 \times 10^8$ |
| VI | 1 | — |

Referring to FIG. 1, around 90% of mice die in 4 days after the infection of $K.$ $pneumoniae$ (as shown in I curve). However, the risk of $K.$ $pneumoniae$ induced death can be significantly reduced by the bacteriophage treatment of the present invention in a positive dose-dependent manner. The mice have treatments of $2 \times 10^6$ (namely $10^5$ PFU/g/day; MOI=0.01), $2 \times 10^7$ (namely $10^6$ PFU/g/day; MOI=0.1) and $2 \times 10^8$ (namely $10^7$ PFU/g/day; MOI=1) PFU/mouse bacteriophage respectively, resulting in approximately 90% of survival in the present invention (see the III, IV and V curve). It is suggested that the bacteriophage of the present invention is sufficient to suppress infection of $K.$ $pneumoniae$. This shows dramatic improvement on the $K.$ $pneumoniae$-induced mice death, also with no risk of any safety problems. Hence, it is believed that the therapy or prophylaxis of $K.$ $pneumoniae$ infections with a lytic bacteriophage specifically against the $K.$ $pneumoniae$ in the present invention is beneficial to treat $K.$ $pneumoniae$ infected organisms.

Figure 2:
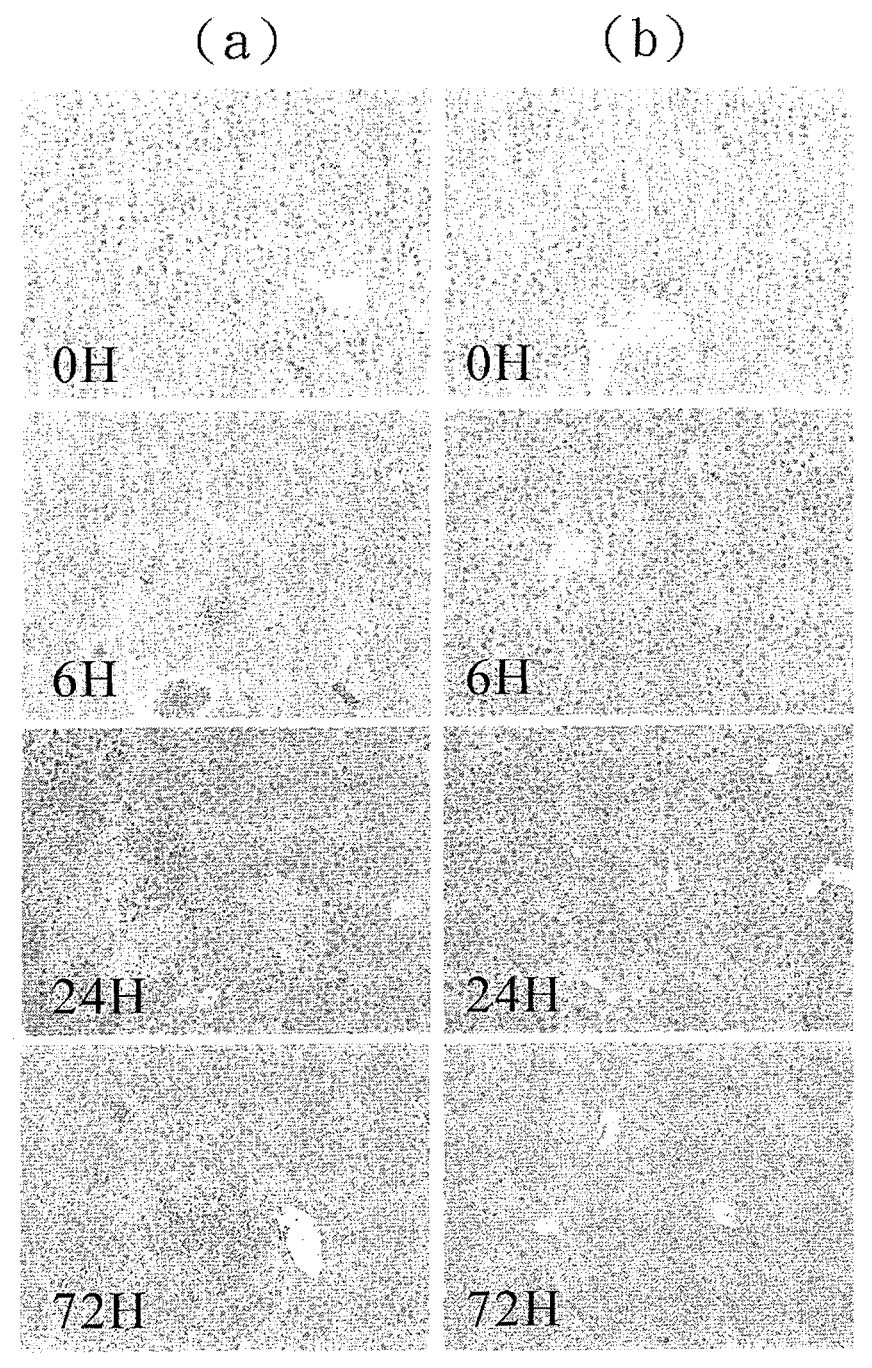

With reference the FIG. 2, in accordance with the analyzed data of histochemistry stain of liver tissue in mice, the mice with $K.$ $pneumoniae$ infection have severe tissue inflammation and necrosis in the liver, especially after 24 hours of infection (see the section a). In contrast, the infected mice receiving the bacteriophage treatment of the present invention only have mild tissue inflammation in the liver (see the section b, 24H). Also the affected parts in these mice make a quick recovery from infection (see the section b, 72H).

Figure 3:
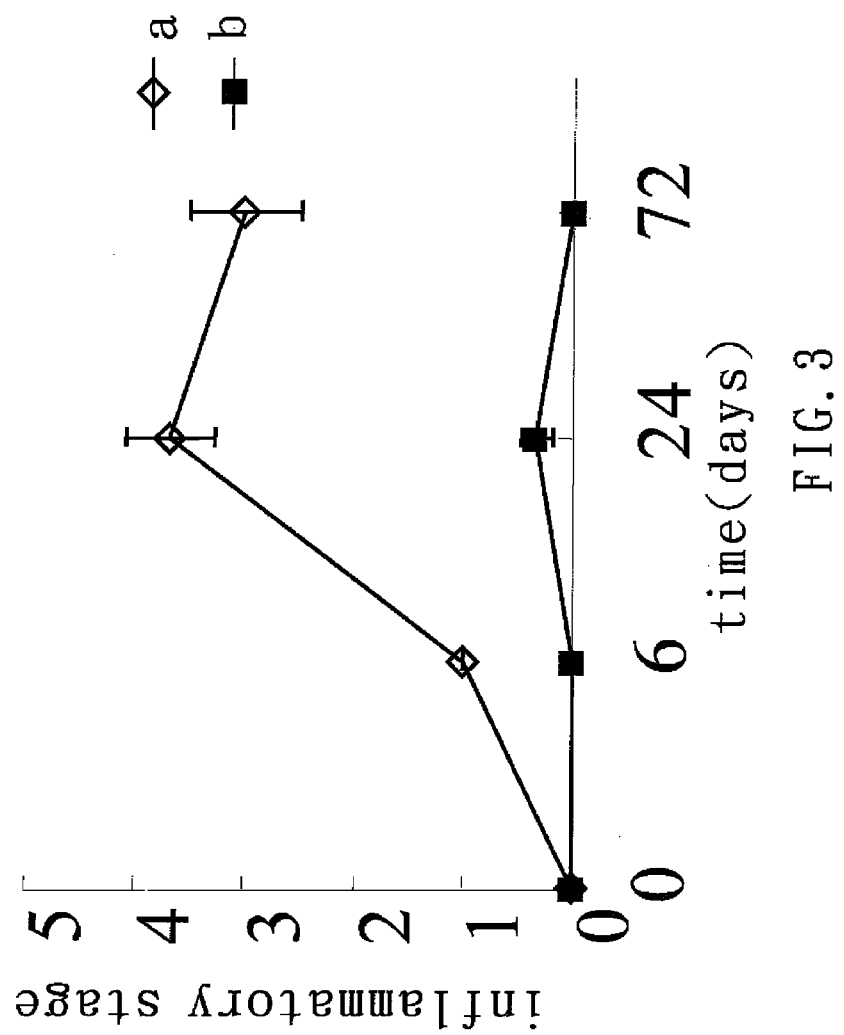
FIG. 3 is a line chart illustrating the inflammatory stage of the liver in infected mice.

Moreover, FIG. 3 summarizes the inflammatory stage of the liver in the above-mentioned mice, wherein the inflammation of liver rapidly develops to stage III in 24 hours in the *K. pneumoniae* infected mice (a). On the other hand, the infected mice receiving the bacteriophage treatment of the present invention (b) only show slight inflammation in the 24 hours of infection and fast recovery from inflammation within 72 hours of infection. Therefore, it is suggested the bacteriophage treatment of the present invention is sufficient to relieve the liver inflammation caused by *K. pneumoniae* infection. Also it can advance the recovery of the inflammatory liver tissue in *K. pneumoniae* infected organisms.

Figure 4:
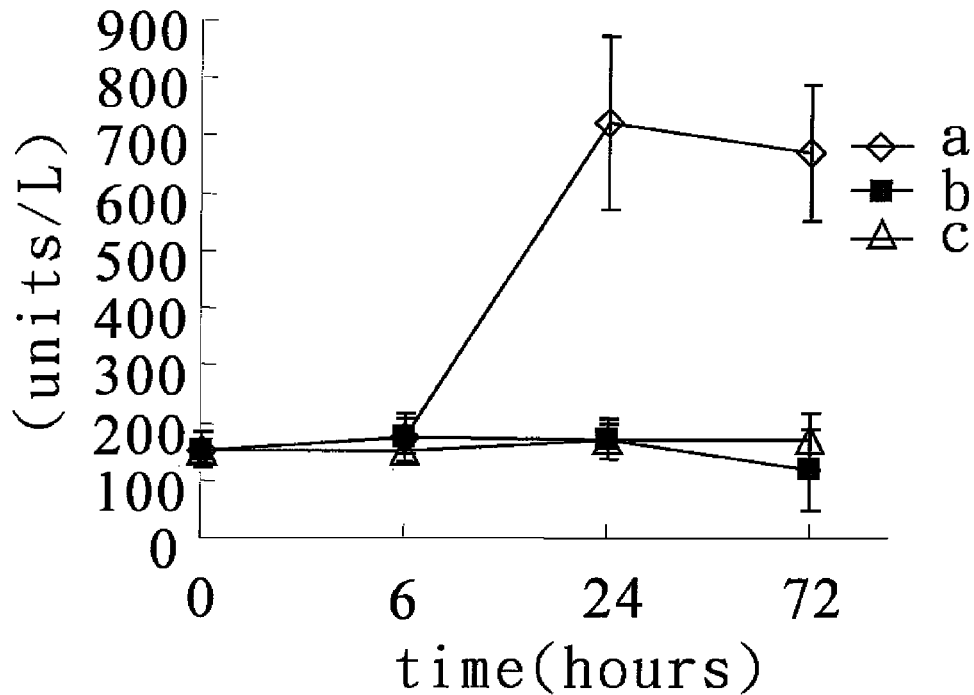
FIG. 4 is a line chart illustrating the concentration of AST of the liver in mice.
Figure 5:
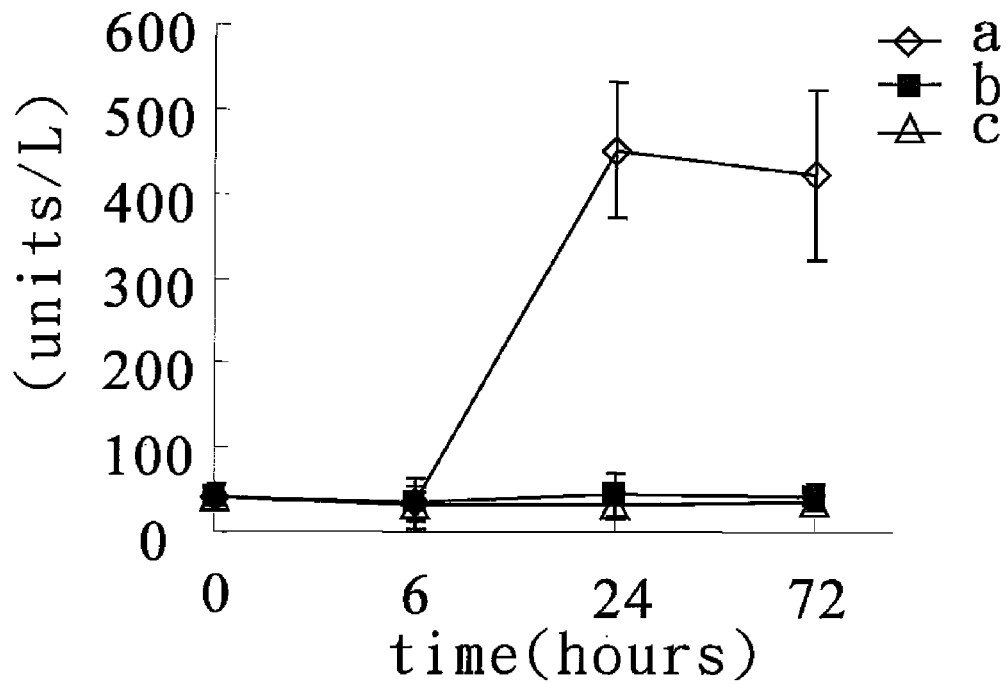
FIG. 5 is a line chart illustrating the concentration of ALT of the liver in mice.

Referring to the FIGS. 4 and 5, the aspartate aminotransferase (also known as AST) and alanine aminotransferase (also known as ALT) levels in partial mice serum are monitored in the embodiment of the present invention, wherein the AST level in the *K. pneumoniae* infected mice increases rapidly to around 700 units/L in 24 hours (see the FIG. 4, curve a), with about 5 times more than the standard value in normal mice. In the infected mice receiving the bacteriophage treatment (b) and the healthy mice only receiving bacteriophage treatment (c), the AST level mainly remains at the standard value, with approximately 150 unit/L (see the FIG. 4, curves b and c). On the other hand, ALT level in the *K. pneumoniae* infected mice also increases to around 450 units/L in 24 hours (see the FIG. 5, curve a), with about 10 times more than the standard value in normal mice. In the infected mice receiving the bacteriophage treatment (b) and the healthy mice only receiving bacteriophage treatment (c), the ALT level mainly remains at the standard value, with approximately 40 units/L (see the FIG. 5, curves b and c). It is indicated that the bacteriophage treatment of the present invention is effective in reducing the *K. pneumoniae*-induced liver abscess in organisms; therefore, the tissue necrosis and inflammation of liver, and the increase of AST and ALT levels in serum are moderated.

As outlined in Table 2, samples of blood and liver are taken from the infected mice with or without a bacteriophage treatment for undergoing a process of bacterial count after 6, 24 and 72 hours of infection, wherein the data of each sample is recorded and summarized below.

TABLE 2 bacterial count in each blood sample and liver sample

| Times | Bacterial count in liver ($\log_{10}$CFU/g) | | Bacterial count in blood ($\log_{10}$CFU/ml) | |
|---|---|---|---|---|
| | a | b | a | b |
| 6 | 2.78 ± 0.34 | <2.5 | 2.10 ± 0.11 | <2 |
| 24 | 6.58 ± 0.09 | <2.5 | 6.06 ± 1.02 | <2 |
| 72 | 5.71 ± 0.21 | <2.5 | 5.74 ± 0.81 | <2 |

It is shown that the infected mice (a) provides a highest amount of bacteria count at 24 hours after infection, with about $10^{6.6}$ CFU/g and $10^6$ CFU/g bacteria in the liver and blood sample, respectively. In contrast, the infected mice with bacteriophage treatment only show less than $10^{2.5}$ CFU/g bacteria either in liver sample or blood sample. Hence, it is suggested that the bacteriophage treatment of the present invention is sufficient to inhibit the reproduction of *K. pneumoniae* in organisms so as to efficiently relieve the *K. pneumoniae* induced bacteremia in organisms.

Figure 6:
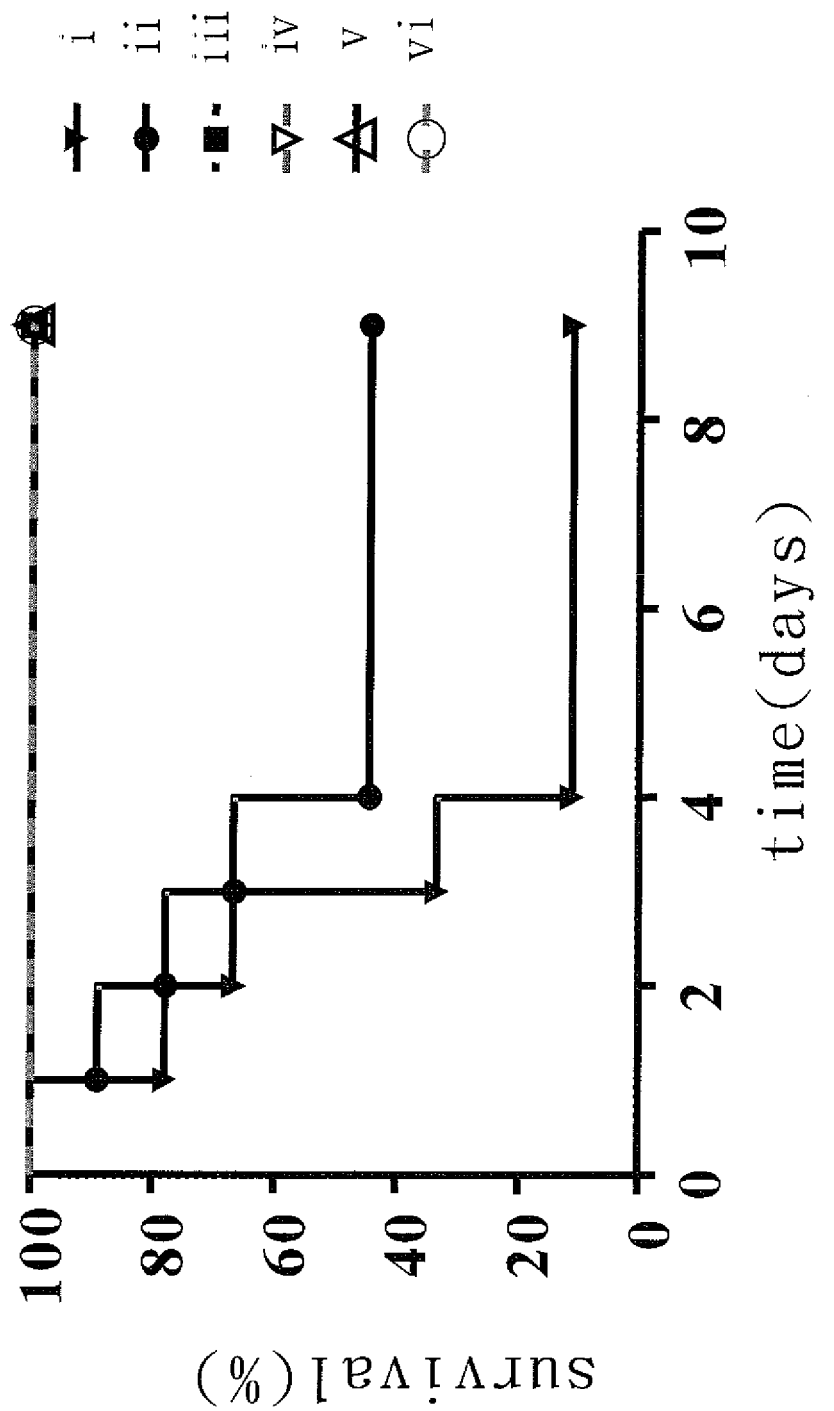
FIG. 6 is a line chart illustrating the survival rate of infected mice with different oral dosages of bacteriophage treatment.

In the embodiment of the present invention, different dosages of the bacteriophage treatment of the present invention is further orally given to the *K. pneumoniae* infected mice, wherein the survival rate of the infected mice are monitored and recorded in FIG. 6. The detailed information about the dosages of the bacteriophage treatment in the present invention is provided in Table 3.

TABLE 3

The dosage of oral bacteriophage treatment in infected mice

| Groups | MOI of the bacteriophage | Titer of *K. pneumoniae* (CFU/mouse) |
|---|---|---|
| i | — | $2 \times 10^8$ |
| ii | 0.001 | $2 \times 10^8$ |
| iii | 0.01 | $2 \times 10^8$ |
| iv | 0.1 | $2 \times 10^8$ |
| v | 1 | $2 \times 10^8$ |
| vi | 1 | — |

With reference to FIG. 6, the *K. pneumoniae* infected mice will die sequentially after 1 day of infection, wherein only a 10% rate of survival exists. On the other hand, the infected mice receiving bacteriophage treatment orally have a significantly higher survival rate than in untreated mice, with about 40%, 100%, 100% and 100% of survival rate in $2 \times 10^5$ PFU/mouse (namely $10^4$ PFU/g/day), $2 \times 10^6$ PFU/mouse (namely $10^5$ PFU/g/day), $2 \times 10^7$ PFU/mouse (namely $10^6$ PFU/g/day) and $2 \times 10^8$ PFU/mouse (namely $10^7$ PFU/g/day) of bacteriophage treated mice, respectively (see the curve ii, iii, iv and v). It is suggested that the bacteriophage treatment delivered orally is sufficient, and performs as well as that delivered via injection, to suppress the infection of the *K. pneumoniae*. This shows dramatic improvement on the *K. pneumoniae*-induced death. Also, there involves no risk of any side effects. Hence, it is proved that the therapy or prophylaxis of *K. pneumoniae* infections with a lytic bacteriophage specifically against the *K. pneumoniae* in the present invention is beneficial to treat the *K. pneumoniae* infected organisms either via an injection approach or an oral approach.

Figure 7:
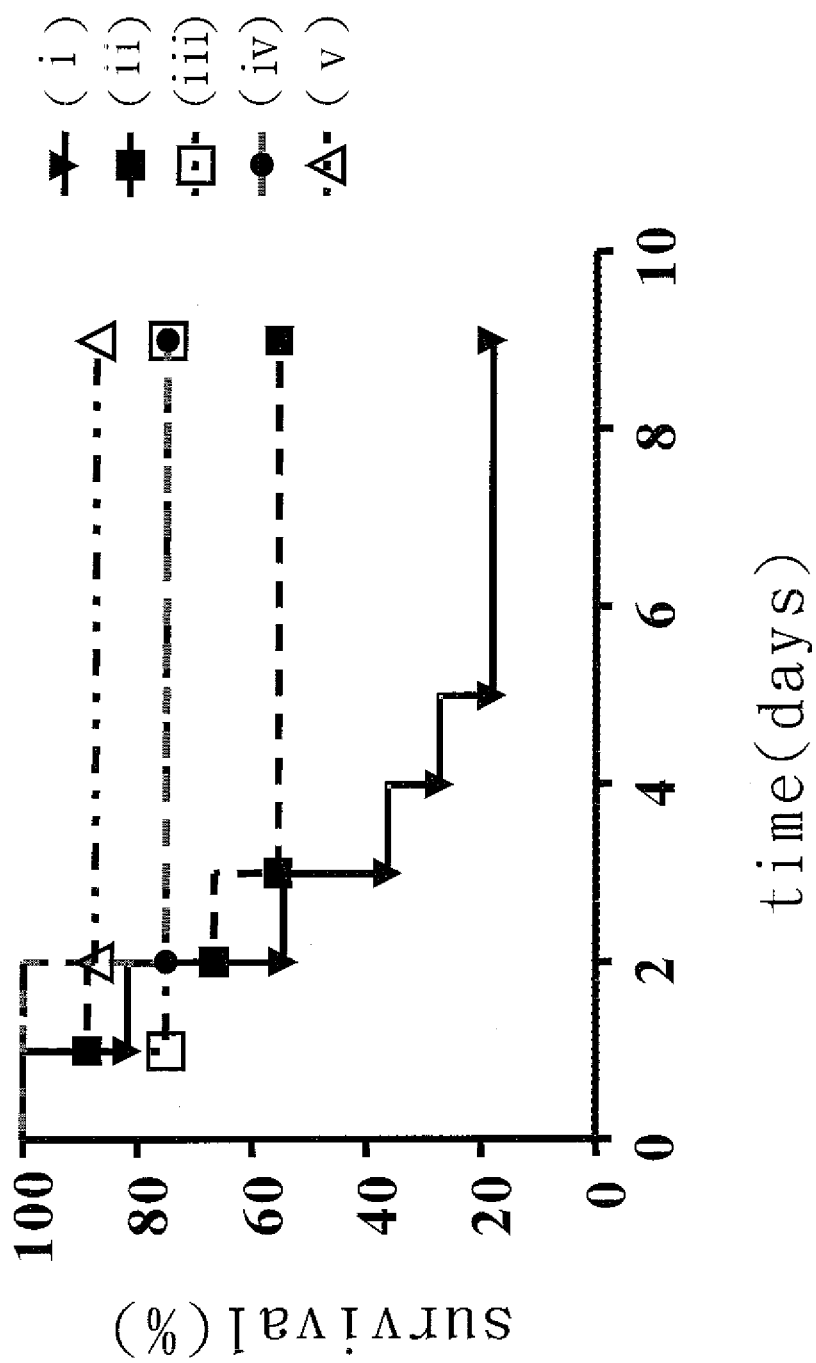
FIG. 7 is another line chart illustrating the survival rate of infected mice with bacteriophage treatment given at different times after infection.

Additionally, with reference to Table 4, the bacteriophage treatment of the present invention is further given to the *K. pneumoniae* infected mice at different times after infection via an oral or intraperitoneal injection approach, wherein the survival rate of the infected mice in each group are monitored and recorded in FIG. 7.

TABLE 4

The delivering approach and delivering time of bacteriophage treatment in each group

| Groups | Titer of *K. pneumoniae* (CFU/mouse) | Delivering time (hours) | Delivering approach |
|---|---|---|---|
| (i) | $2 \times 10^8$ | — | |
| (ii) | $2 \times 10^8$ | 24 | oral |
| (iii) | $2 \times 10^8$ | 24 | injection |
| (iv) | $2 \times 10^8$ | 6 | oral |
| (v) | $2 \times 10^8$ | 6 | injection |

Referring to FIG. 7, the infected mice with bacteriophage treatment all have a higher survival rate compared with the untreated mice, especially to the mice that underwent intraperitoneal treatment of bacteriophage after 6 days of infection (see the curve (v)). Also, the mice receiving bacteriophage treatment orally after 6 and 24 hours of infection have around 75% and 55% of survival rate, respectively. Therefore, it is suggested that the therapy or prophylaxis of *K. pneumoniae* infections with a lytic bacteriophage specifically against the *K. pneumoniae* in the present invention has positive curative effects on the *K. pneumoniae* infected organisms, wherein the bacteriophage treatment is preferably delivered via injection and as early as possible after infection.

In summary, the therapy or prophylaxis of *K. pneumoniae* infections with a lytic bacteriophage specifically against the *K. pneumoniae* of the present invention is efficient in modulating the *K. pneumoniae* infection and its complications of liver abscess and bacteremia in organisms. The bacteriophage treatment of the present invention can be delivered directly or accompanied by other reagents or medications, for example antibiotics, and shows dramatic curative effects on *K. pneumoniae* induced death, as well as on the complications of liver abscess and bacteremia in general organisms.

Through the present invention, a therapy or prophylaxis of *K. pneumoniae* infections with a lytic bacteriophage (with deposit number (DSM 24329) specifically targeted to the *K. pneumoniae* is developed and applied to the *K. pneumoniae* infected organisms. It is proved to have positive effects on the *K. pneumoniae* infected organisms, which is beneficial in suppressing the *K. pneumoniae* infection and its complications in Taiwan, and also in improving the medical quality of Taiwanese hospitals.

Although the invention has been described in detail with reference to its presently preferred embodiment, it will be understood by one of ordinary skill in the art that various modifications can be made without departing from the spirit and the scope of the invention, as set forth in the appended claims.

What is claimed is:

1. A therapeutic method for relieving complications of liver abscesses and bacteremia of *Klebsiella pneumoniae* infections in a patient, the method comprising the step of administering to said patient an isolated lytic bacteriophage, DSM 24329, specific for *Klebsiella pneumonia*.

2. The method for therapy of *K. pneumoniae* infections with a lytic bacteriophage specifically against *K. pneumoniae* as defined in claim 1, wherein a given route of the bacteriophage is via injection.

3. The method for therapy of *K. pneumoniae* infections with a lytic bacteriophage specifically against *K. pneumoniae* as defined in claim 2, wherein a given dosage of the bacteriophage is $10^4$ to $10^7$ (PFU/g/day).

4. The method for therapy of *K. pneumoniae* infections with a lytic bacteriophage specifically against *K. pneumoniae* as defined in claim 1, wherein a given route is oral.

5. The method for therapy of *K. pneumoniae* infections with a lytic bacteriophage specifically against *K. pneumoniae* as defined in claim 4, wherein a dosage of the bacteriophage is $10^4$ to $10^7$ (PFU/g/day).

6. The method for therapy of *K. pneumoniae* infections with a lytic bacteriophage specifically against *K. pneumoniae* as defined in claim 1, wherein the lytic bacteriophage is accompanied with other pharmaceutically acceptable reagents or medications when it is given to the patient.

* * * * *